(12) United States Patent
Saitoh et al.

(10) Patent No.: US 6,835,543 B2
(45) Date of Patent: Dec. 28, 2004

(54) STEP AGGLUTINATION IMMUNOASSAY

(75) Inventors: Kazunori Saitoh, Ryugasaki (JP); Mitsuhisa Manabe, Ryugasaki (JP)

(73) Assignee: Daiichi Pure Chemicals Co., Ltd., Tokyo (JP)

( * ) Notice: Subject to any disclaimer, the term of this patent is extended or adjusted under 35 U.S.C. 154(b) by 0 days.

(21) Appl. No.: 08/893,759

(22) Filed: Jul. 11, 1997

(65) Prior Publication Data

US 2001/0007774 A1 Jul. 12, 2001

(30) Foreign Application Priority Data

Jul. 12, 1996 (JP) ............................................. 8-183279

(51) Int. Cl.$^7$ .............................................. G01N 33/53
(52) U.S. Cl. ...................... 435/7.1; 435/962; 436/518; 436/519; 436/524; 436/527; 436/531; 436/533; 436/534; 436/540
(58) Field of Search .................. 435/7.1, 962; 436/518, 436/519, 524, 527, 531, 533, 534, 540

(56) References Cited

U.S. PATENT DOCUMENTS

| | | | | |
|---|---|---|---|---|
| 4,375,414 A | * | 3/1983 | Strahilevitz | 436/534 |
| 5,180,679 A | * | 1/1993 | Schmidtberger | 436/518 |
| 5,460,947 A | * | 10/1995 | Young et al. | 435/7.92 |
| 5,492,841 A | * | 2/1996 | Craig | 436/534 |

FOREIGN PATENT DOCUMENTS

| | | | |
|---|---|---|---|
| EP | 0 617 285 | | 9/1994 |
| EP | 0 617 285 A | * | 9/1994 |
| WO | WO 85/02258 | | 5/1985 |

OTHER PUBLICATIONS

Cruse et al., "Illustrated Dictionary of Immunology," CRC Press, Boca Raton, 1995, pp. 8–9, "agglutination", 1995.*
Soybel et al. "An Amikacin Latex Agglutination Immunoassay for the IL Multistat® System and Monarch™ Analyzer," Clin. Chem. 32(6) :1084–85, 1986.*
Tietz (ed), "Textbook of Clincal Chemistry," W. B. Saunders Company, Philadelphia, pp 230–231, Agglutination Assays, 1986.*
Derwent Abstract Accession No. 94–295892/199437 of EP617285, 1994.*

* cited by examiner

Primary Examiner—Christopher L. Chin
(74) Attorney, Agent, or Firm—Oblon, Spivak, McClelland, Maier & Neustadt, P.C.

(57) ABSTRACT

An immunoassay for detecting an antigen in a sample, by:
(a) sequentially contacting the sample with
(i) a first antibody which is capable of specifically binding to a first binding site on the antigen, and then
(ii) a second antibody which is capable of specifically binding to a second binding site on the antigen,
thereby forming, when the antigen is present in the sample, an agglutinate comprising the first antibody, the antigen, and the second antibody; followed by
(b) optically measuring the amount of the agglutinate.

28 Claims, 4 Drawing Sheets

STEP AGGLUTINATION IMMUNOASSAY

BACKGROUND OF THE INVENTION

1. Field of the Invention

The present invention relates to a method of determining an antigen in a test specimen, and more particularly to an immunoassay which makes use of agglutination by a two-stage reaction using an insoluble carrier, has high specificity and is simple and low in cost.

2. Description of the Background Art

As immunoassays based on an antigen-antibody reaction, there have heretofore been known assays making use of an agglutination reaction and assays making use of an antibody labeled with an enzyme for detection. In these immunoassays, the amount of an immune complex formed by a specific antigen-antibody reaction is determined either visually or as an optical change. In particular, a method (hereinafter referred to as "agglutination method") of determining an antigen in a test specimen making use of an agglutination reaction or agglutination inhibition reaction based on the antigen-antibody reaction of insolubilized particles (hereinafter referred to as "immobilized antibody") obtained by holding an antibody on an insoluble carrier with an antigen responsive to the antibody permits automating of determination, and so is applied to automatic analyzers and widely spreads.

Many of the agglutination methods heretofore in use employ latex particles as the insoluble carrier, and it is known to react an immobilized antibody using (1) a polyclonal antibody, (2) a kind of monoclonal antibody or (3) two kinds of monoclonal antibodies with an objective antigen in a test specimen to form an immune aggregate, and determine the degree of the agglutination either visually or optically. Besides, there is also known (4) a method in which an objective antigen in a test specimen is adsorbed on or bound to an insoluble carrier, and an antibody responsive to the antigen is then reacted to selectively agglutinate the insoluble carrier (Japanese Patent Application Laid-Open No. 35752/1995).

However, the above-described conventional methods involve the following drawbacks. Namely, the method of (1) is the most commonly used method but involves such problems that the polyclonal antibody cross-reacts to foreign antibodies derived from a trace amount of foreign components contained in an antigen used for antibody formation and to other components similar in structure to the objective antigen because the specificity of an assay system is affected by the specificity of the polyclonal antibody used. The method of (2) can be used only for special antigens in which there are a plurality of parts (hereinafter referred to as "recognition sites") which participate in the antigen-antibody reaction because only a kind of monoclonal antibody is used. According to the method of (3), an immune agglutinate is formed by increasing the number of recognition sites to a number corresponding to the number of antibodies by using two kinds of monoclonal antibodies. However, not that a combination of any two kinds of antibodies may be used so far as they are monoclonal antibodies responsive to the same antigen, but there is a problem that a combination of special two kinds of antibodies must be selected according to an object. Further, the method of (4) involves a problem that the insoluble carrier is non-specifically adsorbed on a reactor of an automatic analyzer, so that the reactor is contaminated.

There is also a method in which an immobilized antibody and a free antibody are used (Japanese Patent Publication No. 31227/1991). However, this method comprises, in a reaction system in which the immobilized antibody reacts to an object of determination to form an optically measurable immune agglutinate, causing both antibodies (the free antibody and immobilized antibody) to compete to the object of determination, thereby inhibiting the occurrence of immune agglutination to enlarge a measuring range. Therefore, this method is different in both principle and object from the present invention in which two antibodies different in form from each other are used in order to cause and increase immune agglutination.

SUMMARY OF THE INVENTION

In view of the above-described problems, the present invention has been made and has as its object the provision of an immunoassay which makes use of agglutination of an immobilized antibody to an object of determination and has high specificity.

In view of the foregoing circumstances, the present inventors have carried out an extensive investigation. As a result, it has been found that two kinds of antibodies, which respectively recognize different sites of an objective antigen of determination, are used and successively reacted in a state that one of them is immobilized, and the other is free, thereby permitting the achievement of an immunoassay which has high specificity and is simple and low in cost, thus leading to completion of the present invention.

According to the present invention, there is thus provided an immunoassay comprising reacting an immobilized antibody obtained by holding an antibody, which recognizes a part of an objective antigen of determination, on insoluble carrier particles with an antigen in a test specimen, then reacting a free antibody, which recognizes an antigen site different from that recognized by the immobilized antibody, with the antigen, and optically determining the degree of a change in agglutination occurred by the reaction.

According to the present invention, there is also provided an immunoassay comprising reacting a free antibody, which recognizes a part of an objective antigen of determination, with an antigen in a test specimen, then reacting an immobilized antibody obtained by holding an antibody, which recognizes an antigen site different from that recognized by the free antibody, on insoluble carrier particles with the antigen, and optically determining the degree of a change in agglutination occurred by the reaction.

The immunoassays according to the present invention have advantages that they have high specificity and are simple and low in cost, and with respect to the antibodies used, insofar as one of the immobilized antibody and the free antibody has high specificity for the objective antigen of determination, the other antibody does not need to have strict specificity and may have some cross-reactivity.

The above and other objects, features, and advantages of the present invention will be readily appreciated from the preferred embodiments of the present invention, which will be described subsequently in detail with reference to the accompanying drawings.

DETAILED DESCRIPTION OF THE PREFERRED EMBODIMENTS

Figure 1:
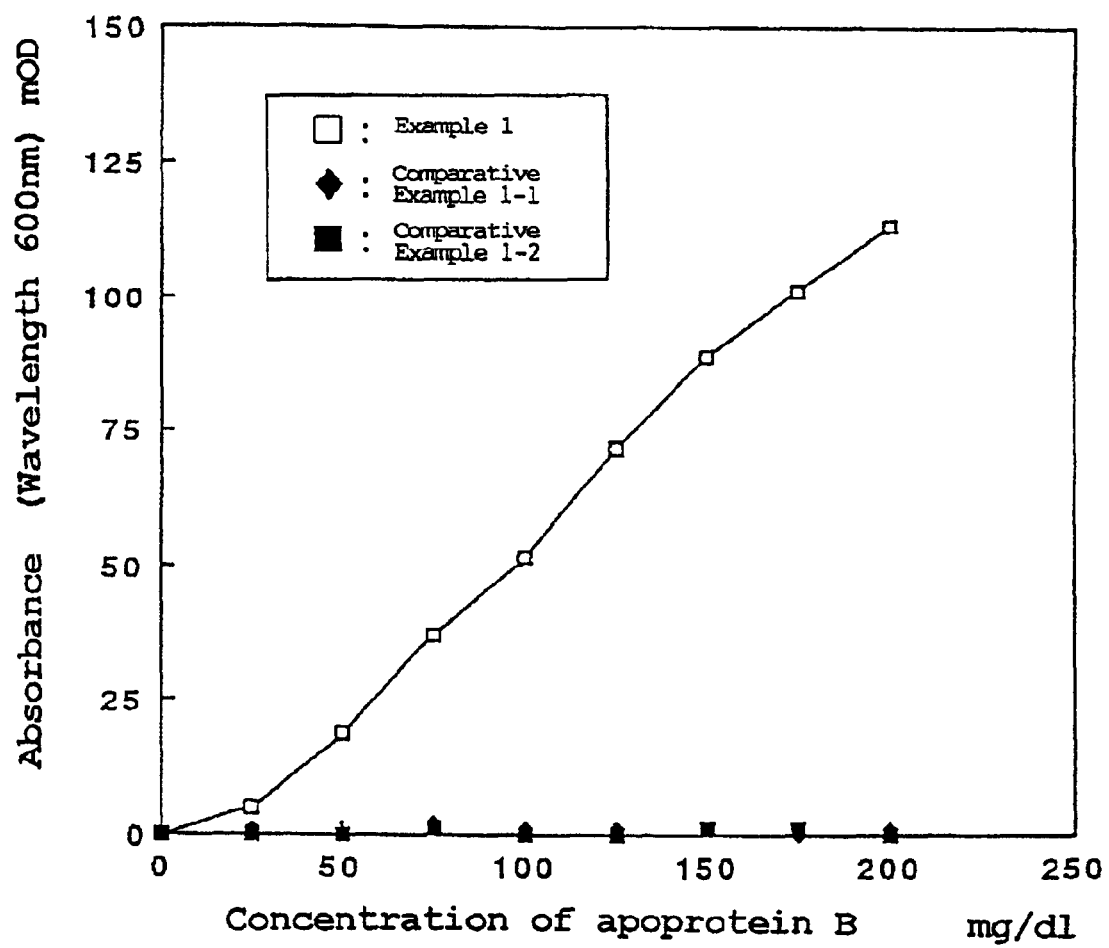
FIG. 1 illustrates a relationship between an absorbance and a concentration of apoprotein B when assaying the apoprotein B according to the present invention.

As the insoluble carrier particles useful in the practice of the present invention, any known substance heretofore used in assaying an antigen or antibody using an insoluble carrier may be used without any limitation. Examples thereof include organic polymeric substances, inorganic substances, cell membranes, hemocytes and microorganisms. Preferable examples of the organic polymeric substances include latex particles obtained by uniformly suspending fine powder of an acrylic acid polymer, styrene polymer, methacrylic acid polymer or the like. Examples of the inorganic substances include fine particles of silica, alumina and the like. No particular limitation is also imposed on the particle size of the insoluble carrier particles. However, the carrier particles preferably have an average particle size of generally 0.05–1 $\mu$m, particularly 0.05–0.5 $\mu$m. Further, no particular limitation is also imposed on the method of immobilizing the antibody on such an insoluble carrier, and examples thereof include physical adsorption, covalent bonding, immunological bonding and magnetic bonding.

No particular limitation is imposed on a liquid suspending the immobilized antibody therein. However, a buffer solution such as a phosphate buffer, glycine buffer, tris buffer or Good buffer is generally used. A pH in the reaction is preferably 5–10, particularly 6–9. No particular limitation is imposed on the concentration of the immobilized antibody in a reagent finally prepared. However, the immobilized antibody is preferably at a concentration of 0.1–10 mg/ml in the suspension.

The forms of the antibodies used in the present invention are two forms of an immobilized antibody and a free antibody. These antibodies may be either monoclonal antibodies or polyclonal antibodies so far as they respectively recognize different sites on an objective antigen of determination. Incidentally, with respect to the antibodies used in the present invention, insofar as one of the immobilized antibody and the free antibody has high specificity for the object of determination, the other antibody does not need to have strict specificity and may have some cross-reactivity. The antibodies may be used either singly or in any combination so far as they satisfy the above-described conditions.

No particular limitation is imposed on the objective antigen of determination in the present invention. However, examples thereof include hormones (insulin, HCG-$\beta$, growth hormone, TSH, LH, FSH, prolactin, thyroxin, triiodothyronine, gastrin, glucagon, somatostatin and the like), enzymes (elastase, amylase, protease, lipase, ribonuclease, enolase, alkaline phosphatase and the like), serum proteins (IgG, IgA, IgM, IgE, IgD, RF, SAA, SLO, macroglobulin, TBG, glycoprotein, glycolipid, apoproteins AI, AII, B, CI, CII, CIII, D, E and F, and the like), clotting-fibrinolytic factors (TAT, PIC, ATIII, APL and the like), HbA$_1$C, tumor-associated antigens (CEA, $\alpha$-fetoprotein, ferritin, POA, CA19-9, CA125 and the like), DNA-binding protein factors, cytokines (interferon, interleukin-1, interleukin-2 and the like), various bacteria, viruses, and protozoa (fungi, streptococci, hepatitis viruses, herpes viruses, AIDS viruses, Toxoplasma gondii, malaria parasites, Entamoeba histolytica and the like).

The determination of the antigen in a test specimen according to the immunoassay of the present invention is performed, for example, in the following manner. Namely, an agglutinate is formed by a two-stage reaction in which the antigen is reacted with the immobilized antibody, and the free antibody is then reacted, or another two-stage reaction in which the antigen is reacted with the free antibody, and the immobilized antibody is then reacted. The reduction in transmitted light depending on the amount of the agglutinate can be determined by a spectrophotometer or an automatic analyzer to measure the amount of the antigen in the specimen by its checking with a calibration curve prepared in advance, or the like.

The principle of the reaction in the present invention is a two-stage reaction that an immobilized antibody or a free antibody is reacted with an objective antigen to capture the antigen by the antibody, and a detectable agglutinate is formed through the free antibody or immobilized antibody capable of coupling with the antigen thus capture. Therefore, the immunoassay according to the present invention is different in reaction mechanism from the conventional agglutinative immunoassay in which immobilized antibody molecules are agglutinated each other at one stage through an objective antigen to form an optically detectable agglutinate. Besides, the immunoassay according to the present invention is greatly different from an immunoturbidimetry in which an antigen-antibody reaction is conducted in the presence of an immune reaction-accelerating component such as polyethylene glycol 6000 to optically determine the degree of immune agglutination in that no immune reaction-accelerating component is required, and the immobilized antibody is used.

The present invention will hereinafter be described in more detail by the following Examples. However, the present invention is not limited to these examples.

EXAMPLE 1

Assay of Apoprotein B
(1) Preparation of a Suspension of an Anti-Apoprotein B Antibody Immobilized on Particles:
Added to 5 ml of a solution obtained by mixing an anti-apoprotein B monoclonal antibody at a concentration of 1.4 mg/ml with a 0.05 M glycine buffer (pH: 8.4) were 5 ml of a 2% suspension of a polystyrene latex (product of Sekisui Chemical Co., Ltd.) having an average particle size of 0.2 µm, followed by stirring at 4° C. for 2 hours. A 0.05 M glycine buffer (pH: 8.4) containing 2% bovine serum albumin was then added, and the resultant mixture was stirred overnight at 4° C. to prepare a suspension of an anti-apoprotein B antibody immobilized on particles.

(2) Preparation of a Solution of a Free Anti-Apoprotein B Antibody:

An anti-apoprotein B polyclonal antibody was mixed at a concentration of 0.2 mg/ml with a 0.05 M glycine buffer (pH: 8.4) to prepare a solution of a free anti-apoprotein B antibody.

(3) Assay of Apoprotein B:

After 5 µl of a specimen solution containing apoprotein B were added to 200 µl of the suspension of the anti-apoprotein B antibody immobilized on particles, and the resultant mixture was warmed at 37° C. for 5 minutes, 200 µl of the solution of the free anti-apoprotein B antibody were added, thereby determining the degree of change in absorbance at a wavelength of 600 nm from 1 minute to 5 minutes after stirring the mixture. The thus-obtained relationship between the absorbance and the concentration of the apoprotein B is illustrated in FIG. 1.

Comparative Example 1-1

Assay of apoprotein B was performed in accordance with the same process in Example 1 (3) except that 200 µl of a 0.05 M glycine buffer were used in place of the suspension of the anti-apoprotein B antibody immobilized on particles. The thus-obtained degree of change in absorbance is illustrated in FIG. 1.

Comparative Example 1-2

Assay of apoprotein B was performed in accordance with the same process in Example 1 (3) except that 200 µl of a 0.05 M glycine buffer were used in place of the solution of the free anti-apoprotein B antibody. The thus-obtained degree of change in absorbance is illustrated in FIG. 1.

As apparent from FIG. 1, it is understood that changes in absorbance depending on the concentration of the apoprotein B are observed in Example 1, while no change is recognized in both Comparative Examples 1–1 and 1-2.

EXAMPLE 2

Assay of a Serum Amyloid A Protein (SAA)

(1) Preparation of a Suspension of an Anti-Amyloid A Protein Antibody Immobilized on Particles:

Added to 5 ml of a solution obtained by mixing an anti-amyloid A protein polyclonal antibody at a concentration of 2.8 mg/ml with a 0.05 M glycine buffer (pH: 8.4) were 5 ml of a 2% suspension of a polystyrene latex (product of Sekisui Chemical Co., Ltd.) having an average particle size of 0.2 µm, followed by stirring at 4° C. for 2 hours. A 0.05 M glycine buffer (pH: 8.4) containing 2% bovine serum albumin was then added, and the resultant mixture was stirred overnight at 4° C. to prepare a suspension of an anti-amyloid A protein antibody immobilized on particles.

(2) Preparation of a Solution of a Free Anti-Serum Amyloid A Protein Antibody:

A C-terminal specific anti-serum amyloid A protein polyclonal antibody prepared by immunizing a rabbit with a C-terminal portion of a serum amyloid A protein was mixed at a concentration of 0.5 mg/ml with a 0.05 M glycine buffer (pH: 8.4) to prepare a solution of a free anti-serum amyloid A protein antibody.

Figure 2:
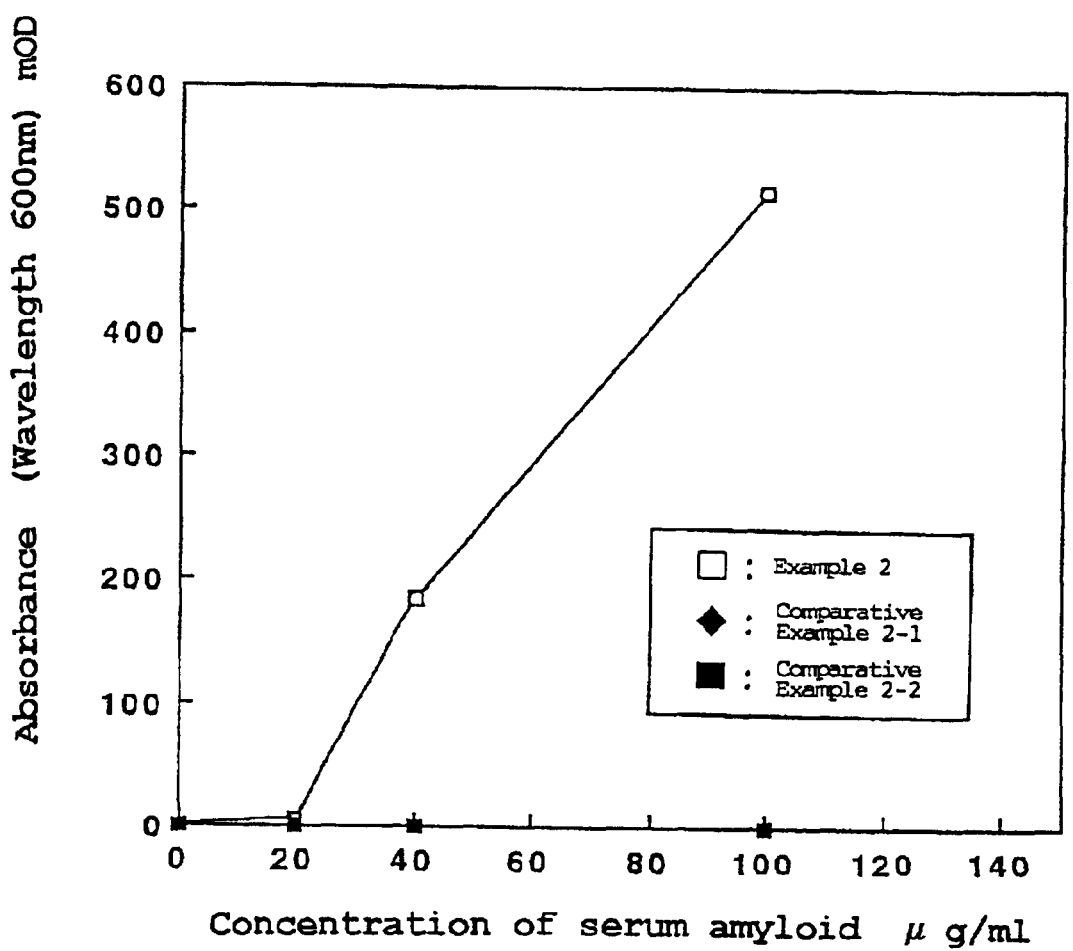
FIG. 2 illustrates a relationship between an absorbance and a concentration of a serum amyloid A protein (SAA) when assaying the SAA according to the present invention.

(3) Assay of a Serum Amyloid A Protein:

After 4 µl of a specimen solution containing a serum amyloid A protein were added to 240 µl of the suspension of the anti-amyloid A protein antibody immobilized on particles, and the resultant mixture was warmed at 37° C. for 5 minutes, 80 µl of the solution of the free anti-serum amyloid A protein antibody were added, thereby determining the degree of change in absorbance at a wavelength of 600 nm from 1 minute to 5 minutes after stirring the mixture. The thus-obtained relationship between the absorbance and the concentration of the serum amyloid A protein is illustrated in FIG. 2.

Comparative Example 2-1

Assay of a serum amyloid A protein was performed in accordance with the same process in Example 2 (3) except that 240 µl of a 0.05 M glycine buffer were used in place of the suspension of the anti-amyloid A protein antibody immobilized on particles. The thus-obtained degree of change in absorbance is illustrated in FIG. 2.

Comparative Example 2-2

Assay of a serum amyloid A protein was performed in accordance with the same process in Example 2 (3) except that 80 µl of a 0.05 M glycine buffer were used in place of the solution of the free anti-serum amyloid A protein antibody. The thus-obtained degree of change in absorbance is illustrated in FIG. 2.

As apparent from FIG. 2, it is understood that changes in absorbance depending on the concentration of the serum amyloid A protein are observed in Example 2, while no change is recognized in both Comparative Examples 2–1 and 2-2.

EXAMPLE 3

Assay of Thrombin-Antithrombin III Complex (TAT)

(1) Preparation of a Suspension of an Anti-Thrombin Antibody Immobilized on Particles:

Added to 5 ml of a solution obtained by mixing an anti-thrombin monoclonal antibody at a concentration of 1.4 mg/ml with a 0.05 M glycine buffer (pH: 8.4) were 5 ml of a 2% suspension of a polystyrene latex (product of Sekisui Chemical Co., Ltd.) having an average particle size of 0.2 µm, followed by stirring at 4° C. for 2 hours. A 0.05 M glycine buffer (pH: 8.4) containing 2% bovine serum albumin was then added, and the resultant mixture was stirred overnight at 4° C. to prepare a suspension of an anti-thrombin antibody immobilized on particles.

(2) Preparation of a Solution of a Free Anti-Antithrombin III Antibody:

An anti-antithrombin III monoclonal antibody was mixed at a concentration of 0.2 mg/ml with a 0.05 M glycine buffer (pH: 8.4) to prepare a solution of a free anti-antithrombin antibody.

Figure 3:
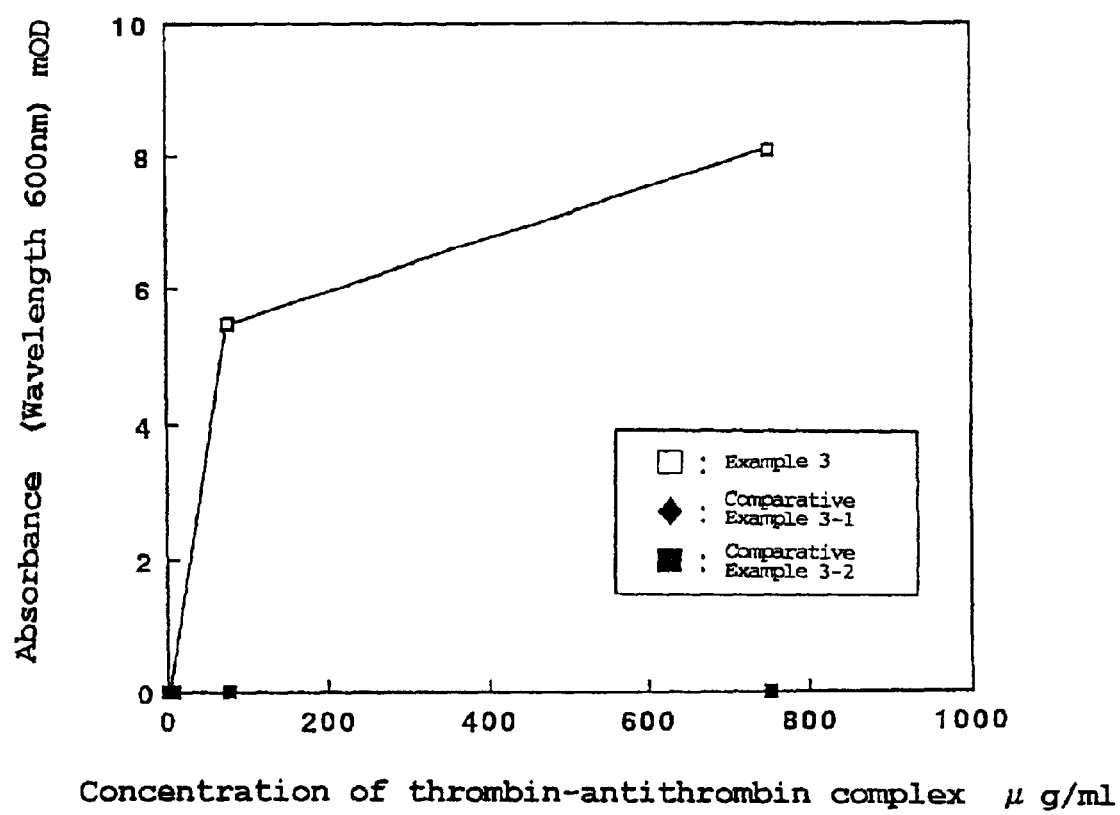
FIG. 3 illustrates a relationship between an absorbance and a concentration of a thrombin-antithrombin complex (TAT) when assaying the TAT according to the present invention.

(3) Assay of a thrombin-antithrombin III complex:

After 20 µl of a specimen solution containing a thrombin-antithrombin III complex were added to 200 µl of the suspension of the anti-thrombin antibody immobilized on particles, and the resultant mixture was warmed at 37° C. for 5 minutes, 100 µl of the solution of the free anti-antithrombin III antibody were added, thereby determining the degree of change in absorbance at a wavelength of 600 nm from 1 minute to 5 minutes after stirring the mixture. The thus-obtained relationship between the absorbance and the concentration of the thrombin-antithrombin III complex is illustrated in FIG. 3.

Comparative Example 3-1

Assay of a thrombin-antithrombin III complex was performed in accordance with the same process in Example 3 (3) except that 200 µl of a 0.05 M glycine buffer were used in place of the suspension of the anti-thrombin antibody immobilized on particles. The thus-obtained degree of change in absorbance is illustrated in FIG. 3.

Comparative Example 3-2

Assay of a thrombin-antithrombin III complex was performed in accordance with the same process in Example 3 (3) except that 100 µl of a 0.05 M glycine buffer were used in place of the solution of the free antiantithrombin III complex antibody. The thus-obtained degree of change in absorbance is illustrated in FIG. 3.

As apparent from FIG. 3, it is understood that changes in absorbance depending on the concentration of the thrombin-antithrombin III complex are observed in Example 3, while no change is recognized in both Comparative Examples 3–1 and 3-2.

EXAMPLE 4

Assay of Thrombin-Antithrombin III Complex (TAT)

(1) Preparation of a Suspension of an Anti-Thrombin Antibody Immobilized on Particles:

Added to 5 ml of a solution obtained by mixing an anti-thrombin monoclonal antibody at a concentration of 1.4 mg/ml with a 0.05 M glycine buffer (pH: 8.4) were 5 ml of a 2% suspension of a polystyrene latex (product of Sekisui Chemical Co., Ltd.) having an average particle size of 0.2 µm, followed by stirring at 4° C. for 2 hours. A 0.05 M glycine buffer (pH: 8.4) containing 2% bovine serum albumin was then added, and the resultant mixture was stirred overnight at 4° C. to prepare a suspension of an anti-thrombin antibody immobilized on particles.

(2) Preparation of a Solution of a Free Anti-Antithrombin III antibody:

An anti-antithrombin III monoclonal antibody was mixed at a concentration of 0.2 mg/ml with a 0.05 M glycine buffer (pH: 8.4) to prepare a solution of a free anti-antithrombin antibody.

Figure 4:
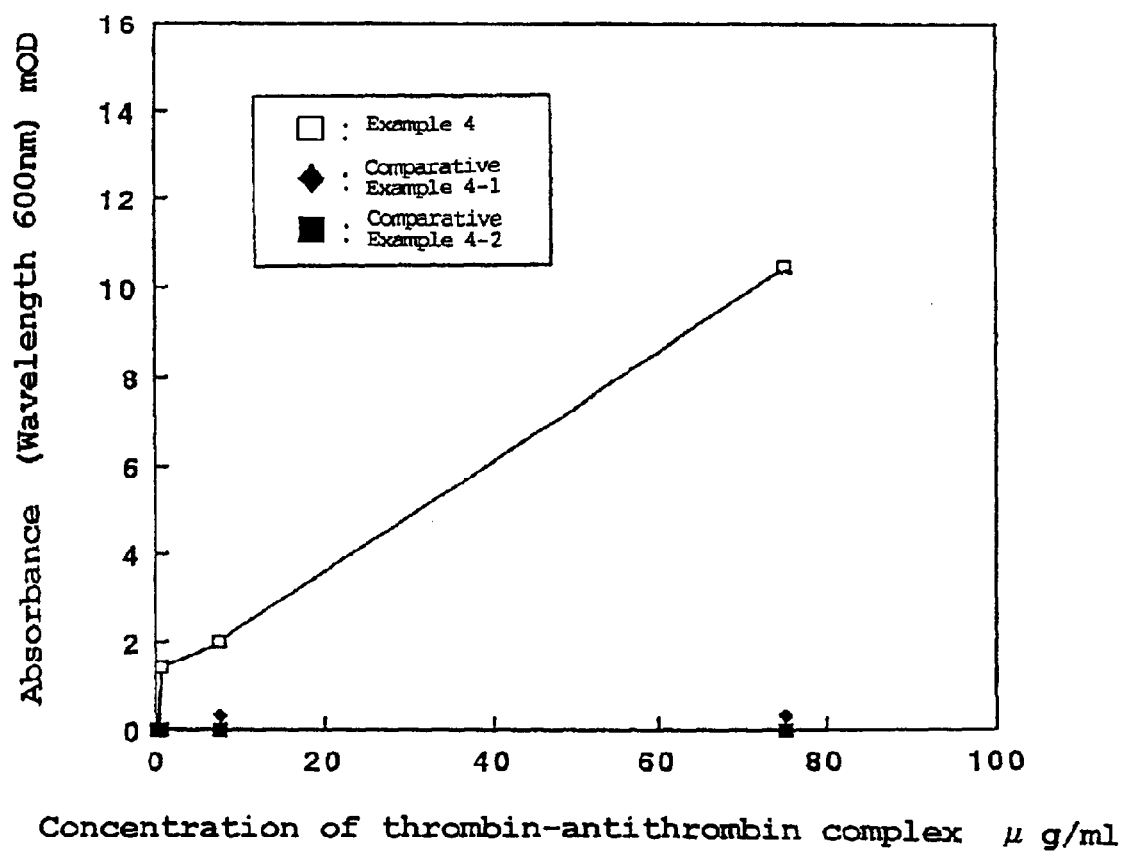
FIG. 4 illustrates a relationship between an absorbance and a concentration of a thrombin-antithrombin complex (TAT) when assaying the TAT according to the present invention.

(3) Assay of a Thrombin-Antithrombin III Complex:

After 20 µl of a specimen solution containing a thrombin-antithrombin III complex were added to 200 µl of the solution of the free anti-antithrombin III antibody, and the resultant mixture was warmed at 37° C. for 5 minutes, 100 µl of the suspension of the anti-thrombin antibody immobilized on particles were added, thereby determining the degree of change in absorbance at a wavelength of 600 nm from 1 minute to 5 minutes after stirring the mixture. The thus-obtained relationship between the absorbance and the concentration of the thrombin-antithrombin III complex is illustrated in FIG. 4.

Comparative Example 4-1

Assay of a thrombin-antithrombin III complex was performed in accordance with the same process in Example 4 (3) except that 200 µl of a 0.05 M glycine buffer were used in place of the solution of the free anti-antithrombin III complex antibody. The thus-obtained degree of change in absorbance is illustrated in FIG. 4.

Comparative Example 4-2

Assay of a thrombin-antithrombin III complex was performed in accordance with the same process in Example 4 (3) except that 100 µl of a 0.05 M glycine buffer were used in place of the suspension of the anti-thrombin antibody immobilized on particles. The thus-obtained degree of change in absorbance is illustrated in FIG. 4.

As apparent from FIG. 4, it is understood that changes in absorbance depending on the concentration of the thrombin-antithrombin III complex are observed in Example 4, while no change is recognized in both Comparative Examples 4–1 and 4-2.

What is claimed is:

1. An agglutination immunoassay for detecting an antigen in a sample, comprising:
    (a) sequentially contacting the sample with
        (i) a first antibody which is capable of specifically binding to a first binding site on the antigen, wherein the first antibody is immobilized on an insoluble carrier, and then
        (ii) a second antibody which is capable of specifically binding to a second binding site on the antigen, wherein the second antibody is free,
    thereby forming, when the antigen is present in the sample, an agglutinate comprising the first antibody, the antigen, and the second antibody; followed by
    (b) optically measuring the amount of the agglutinate formed in (a); followed by
    (c) correlating the amount of agglutinate formed with the amount of the antigen in the sample,
    wherein the antigen is apoprotein B, HbA1C, serum amyloid A protein, or thrombin-antithrombin III complex.

2. The immunoassay of claim 1, wherein said optically measuring comprises spectrophotometrically measuring decreasing light transmission due to formation of the agglutinate.

3. The immunoassay according to claim 1, wherein the amount of the antigen in the sample is determined from a calibration curve.

4. The immunoassay of claim 1, wherein the sample contains an undetectable amount of the antigen.

5. The immunoassay of claim 1, wherein the sample contains a detectable quantity of the antigen.

6. The immunoassay of claim 1, wherein the insoluble carrier is selected from the group consisting of organic polymeric substances, inorganic substances, cell membranes, hemocytes and microorganisms.

7. The immunoassay according to claim 1, wherein the insoluble carrier is a latex particle.

8. The immunoassay of claim 1, wherein the insoluble carrier is silica or alumina.

9. The immunoassay of claim 1, wherein the insoluble carrier has an average particle size of 0.05 to 1 µm.

10. The immunoassay of claim 1, wherein the sample is a buffered aqueous solution.

11. The immunoassay of claim 1, wherein the sample does not contain an immune reaction-accelerating component.

12. The immunoassay of claim 11, wherein the immune reaction-accelerating component is polyethylene glycol 6000.

13. The immunoassay of claim 11, wherein the first antibody is a monoclonal antibody and the second antibody is a polyclonal antibody.

14. An agglutination immunoassay for detecting an antigen in a sample, comprising:
 (a) sequentially contacting the sample with
  (i) a first antibody which is capable of specifically binding to a first binding site on the antigen, wherein the first antibody is free, and then
  (ii) a second antibody which is capable of specifically binding to a second binding site on the antigen, wherein the second antibody is immobilized on an insoluble carrier,
 thereby forming, when the antigen is present in the sample, an agglutinate comprising the first antibody, the antigen, and the second antibody; followed by
 (b) optically measuring the amount of the agglutinate formed In (a); followed by
 (c) correlating the amount of agglutinate formed with the amount of the antigen in the sample,
 wherein the antigen is apoprotein B, HbA1C, serum amyloid A protein, or thrombin-antithrombin III complex.

15. The immunoassay of claim 14, wherein said optically measuring comprises spectrophotometrically measuring decreasing light transmission due to formation of the agglutinate.

16. The immunoassay according to claim 14, wherein the amount of the antigen in the sample is determined from a calibration curve.

17. The immunoassay of claim 14, wherein the sample contains an undetectable amount of the antigen.

18. The immunoassay of claim 14, wherein the sample contains a detectable quantity of the antigen.

19. The immunoassay of claim 14, wherein the insoluble carrier is selected from the group consisting of organic polymeric substances, inorganic substances, cell membranes, hemocytes and microorganisms.

20. The immunoassay according to claim 14, wherein the insoluble carrier is a latex particle.

21. The immunoassay of claim 14, wherein the insoluble carrier is silica or alumina.

22. The immunoassay of claim 14, wherein the insoluble carrier has an average particle size of 0.05 to 1 µm.

23. The immunoassay of claim 14, wherein the sample is a buffered aqueous solution.

24. The immunoassay of claim 14, wherein the sample does not contain an immune reaction-accelerating component.

25. The immunoassay of claim 24, wherein the immune reaction-accelerating component is polyethylene glycol 6000.

26. The immunoassay of claim 14, wherein the first antibody is a monoclonal antibody and the second antibody is a polyclonal antibody.

27. The immunoassay of claim 1, wherein the antigen is apoprotein B.

28. The immunoassay of claim 14, wherein the antigen is apoprotein B.

* * * * *